(12) United States Patent
Boughorbel et al.

(10) Patent No.: US 8,704,176 B2
(45) Date of Patent: Apr. 22, 2014

(54) CHARGED PARTICLE MICROSCOPE PROVIDING DEPTH-RESOLVED IMAGERY

(71) Applicant: FEI Company, Hillsboro, OR (US)

(72) Inventors: Faysal Boughorbel, Eindhoven (NL); Eric Gerardus Theodoor Bosch, Eindhoven (NL); Pavel Potocek, Eindhoven (NL); Xiaodong Zhuge, Tilburg (NL); Berend Helmerus Lich, Weert (NL)

(73) Assignee: FEI Company, Hillsboro, OR (US)

( * ) Notice: Subject to any disclaimer, the term of this patent is extended or adjusted under 35 U.S.C. 154(b) by 0 days.

(21) Appl. No.: 13/856,899

(22) Filed: Apr. 4, 2013

(65) Prior Publication Data
US 2013/0228683 A1 Sep. 5, 2013

Related U.S. Application Data

(63) Continuation-in-part of application No. 13/572,449, filed on Aug. 10, 2012, now Pat. No. 8,586,921, and a continuation-in-part of application No. 13/572,206, filed on Aug. 10, 2012, now Pat. No. 8,581,189.

(60) Provisional application No. 61/758,625, filed on Jan. 30, 2013, provisional application No. 61/620,843, filed on Apr. 5, 2012, provisional application No. 61/522,177, filed on Aug. 10, 2011.

(30) Foreign Application Priority Data

Aug. 10, 2011 (EP) .................................... 11177091
Apr. 5, 2012 (EP) .................................... 12163262
Jan. 30, 2013 (EP) .................................... 13153164

(51) Int. Cl.
*H01J 37/26* (2006.01)

(52) U.S. Cl.
USPC ............ 250/310; 250/306; 250/307; 250/311

(58) Field of Classification Search
USPC .................................. 250/306, 307, 310, 311
See application file for complete search history.

(56) References Cited

U.S. PATENT DOCUMENTS 5,412,210 A 5/1995 Todokoro et al.
6,498,345 B1 12/2002 Weimer et al.
(Continued)

OTHER PUBLICATIONS

Dreomova, N.N., et al., "Characterization of multilayer microstructures and surface relief using backscattered electrons in a scanning electron microscope," Bulletin of the Russian Academy of Sciences—Physics, Jan. 1, 1993, pp. 1305-1310, vol. 57, No. 8.

(Continued)

*Primary Examiner* — Michael Logie
(74) *Attorney, Agent, or Firm* — Scheinberg & Associates, PC; Michael O. Scheinberg; John B. Kelly

(57) ABSTRACT

A method of examining a sample using a charged-particle microscope, comprising mounting the sample on a sample holder; using a particle-optical column to direct at least one beam of particulate radiation onto a surface S of the sample, thereby producing an interaction that causes emitted radiation to emanate from the sample; using a detector arrangement to detect at least a portion of said emitted radiation, the method of which comprises embodying the detector arrangement to detect electrons in the emitted radiation; recording an output $O_n$ of said detector arrangement as a function of kinetic energy $E_n$ of said electrons, thus compiling a measurement set $M=\{(O_n, E_n)\}$ for a plurality of values of $E_n$; using computer processing apparatus to automatically deconvolve the measurement set M and spatially resolve it into a result set $R=\{(V_k, L_k)\}$, in which a spatial variable V demonstrates a value $V_k$ at an associated discrete depth level $L_k$ referenced to the surface S, whereby n and k are members of an integer sequence, and spatial variable V represents a physical property of the sample as a function of position in its bulk.

20 Claims, 5 Drawing Sheets

(56) References Cited

U.S. PATENT DOCUMENTS

| | | | |
|---|---|---|---|
| 6,664,552 B2 | 12/2003 | Shichi et al. | |
| 6,794,663 B2 | 9/2004 | Shichi et al. | |
| 7,268,356 B2 | 9/2007 | Shichi et al. | |
| 7,897,936 B2 | 3/2011 | Shichi et al. | |
| 8,232,523 B2 | 7/2012 | Boughorbel et al. | |
| 8,461,527 B2 | 6/2013 | Nakahira et al. | |
| 8,586,921 B2 * | 11/2013 | Boughorbel et al. | 250/310 |
| 2003/0132382 A1 | 7/2003 | Sogard | |
| 2006/0043291 A1 * | 3/2006 | Peng | 250/310 |
| 2009/0078868 A1 | 3/2009 | de Jonge | |
| 2011/0187847 A1 * | 8/2011 | Bai et al. | 348/80 |
| 2011/0266440 A1 | 11/2011 | Boughorbel et al. | |
| 2012/0049060 A1 | 3/2012 | Luecken et al. | |
| 2012/0097848 A1 | 4/2012 | Lifshin et al. | |
| 2013/0037714 A1 | 2/2013 | Boughorbel et al. | |
| 2013/0037715 A1 | 2/2013 | Boughorbel et al. | |

OTHER PUBLICATIONS

Gostev, A.V., et al., 'Information depth of the backreflected electron mode in scanning electron microscopy,' Bulletin of the Russian Academy of Sciences—Physics, Jan. 1, 1998, pp. 475-480, vol. 62, No. 3.

Niedrig, H., et al., 'Information depth and spatial resolution in BSE microtomography in SEM,' Nuclear Instruments and Methods in Physics Research B, Aug. 1, 1998, pp. 523-534, vol. 142, No. 4.

Alimov, V. KH., et al., 'Depth distribution of deuterium in single- and polycrystalline tungsten up to depths of several micrometers,' Journal of Nuclear Materials, Mar. 1, 2005, pp. 619-623, vol. 337-339.

Ditsman, S.A., et al., 'Stereomicrotomography as a New Method of Scanning Electron Microscopy Investigation of Three-Dimensional Microstructures,' Journal of Surface Investigation, Jan. 1, 2001, pp. 1841-1844, vol. 16, No. 12.

'Site-Specific Cross-Sectioning,' Introduction to Focused Ion Beams, Jan. 1, 2004, pp. 250-255.

Pezzotti, Giuseppe, et al., 'Spatially resolved residual stress assessments of GaN film on sapphire substrate by cathodoluminescence piezospectroscopy,' Journal of Applied Physics, Jul. 21, 2008, pp. 23514-23514, vol. 104, No. 2.

Sato, Kazuhisa, et al., 'Three-dimensional shapes and distribution of FePd nanoparticles observed by electrontomography using high-angle annular dark-field scanning transmission electron microscopy,' Journal of Applied Physics, Jan. 20, 2010, pp. 24304-24304, vol. 107, No. 2.

Sokolov, V.N., et al., 'Analysis of SEM stereoscopic images,' Bulletin of the Russian Academy of Sciences: Physics, 1996, pp. 208-215, vol. 60, No. 2.

Van Den Broek, W., et al., 'A model based reconstruction technique for depth sectioning with scanning transmission electron microscopy,' Ultramicroscopy, Apr. 1, 2010, vol. 110, No. 5.

Xhu, Wenliang, et al., 'Spatially resolved crack-tip stress analysis in semiconductor by cathodoluminescence piezospectroscopy,' Journal of Applied Physics, May 30, 2007, pp. 8-11, vol. 101, No. 10.

Alimov, V.KH., et al., "Depth distribution of deuterium in single- and polycrystalline tungsten up to depths of several micrometers," Journal of Nuclear Material, Mar. 2005, pp. 619-623, vol. 337-339.

Cichocki, Andrzej, et al., "Families of Alpha-Beta- and Gamma-Divergences: Flexible and Robust Measures of Similarities," Entropy, 2010, pp. 1532-1568, vol. 12.

Cichocki, Andrzej, et al., "Generalized Alpha-Beta Divergences and Their Application to Robust Nonnegative Matrix Factorization," Entropy, 2011, pp. 134-170, vol. 13.

Lanteri, Henri, et al., "Penalized maximum likelihood image restoration with positivity constraints: multiplicative algorithms." Inverse Problems, 2002, pp. 1397-1419, vol. 18.

Pezzotti, Giuseppe, et al., "Spatially resolved residual stress assessments of GaN film on sapphire substrate by cathodoluminescence piezospectroscopy," Journal of Applied Physics, Jul. 2008, 12 pgs, vol. 104, No. 2.

Press, William, et al., "Numerical Recipes in C: The Art of Scientific Computing," 1992, pp. 418-479, 2 ed., Cambridge University Press.

Richardson, William, Hadley, "Bayesian-Based Iterative Method of Image Restoration," Journal of the Optical Society of America, Jan. 1972, pp. 55-59, vol. 62, No. 1.

Donolato, C., 'An Analytical Model of SEM and STEM Charge Collection Images of Dislocations in Thin Semiconductor Layers: I. Minority carrier generation, diffusion, and collection' Physica Status Solidi (A), Jun. 16, 1981, pp. 649-658, vol. 65, No. 2.

Shepp, L.A., et al., "Maximum Likelihood Reconstruction for Emission Tomography," IEEE Transaction on Medical Imaging, Oct. 1982, pp. 113-122, vol. MI-1, No. 2.

Unknown, "Bhattacharyya distance." Website, http://en.wikipedia.org/wiki/Bhattacharyya_distance, Publication date unknown, Retrieved Nov. 9, 2012, 3 Pages.

Unknown, "Bregman divergence." Website, http://en.wikipedia.org/wiki/Bregman_divergence, Publication date unknown, Retrieved Nov. 9, 2012, 4 Pages.

Unknown, "Cramer-Rao bound." Website, http://en.wikipedia.org/wiki/Cramer-Roa_bound, Publication date unknown, Retrieved Nov. 9, 2012, 9 Pages.

Unknown, "Expectation-maximization algorithm." Website, http://en.wikipedia.org/wiki/Expectation-maximization_algorithm, Publication date unknown, Retrieved Nov. 9, 2012, 12 Pages.

Unknown, "f-divergence." Website, http://en.wikipedia.org/wiki/F-divergence, Publication date unknown, Retrieved Nov. 9, 2012, 3 Pages.

Unknown, "Finite element method." Website, http://en.wikipedia.org/wiki/Finite_element_method, Publication date unknown, Retrieved Nov. 9, 2012, 14 Pages.

Unknown, "Kullback-Leibler divergence." Website, http://en.wikipedia.org/wiki/Kullback-Leibler_divergence, Publication date unknown, Retrieved Nov. 9, 2012, 14 Pages.

Unknown, "Least squares." Website, http://en.wikipedia.org/wiki/Least_squares, Publication date unknown, Retrieved Nov. 9, 2012, 11 Pages.

Unknown, "Mathematical optimization." Website, http://en.wikipedia.org/wiki/Mathematical_optimization, Publication date unknown, Retrieved Nov. 9, 2012, 15 Pages.

Unknown, "Monte Carlo method." Website, http://en.wikipedia.org/wiki/Monte_Carlo_method, Publication date unknown, Retrieved Nov. 9, 2012, 14 Pages.

Wenliang, Zhu, et al., 'Spatially resolved crack-tip stress analysis in semiconductor by cathodoluminescence piezospectroscopy,' Journal of Applied Physics, May 30, 2007, pgs. vol. 101, No. 10.

Dong, Wende, et al., 'A piecewise local regularized Richardson-Lucy algorithm for remote sensing image deconvolution,' Optics & Laser Technology, Dec. 30, 2010, pp. 926-933, vol. 43.

Gordon, Richard, et al., 'Algebraic Reconstruction Techniques (ART) for Three-dimensional Electron Microscopy and X-Ray Photography,' J. theor. Biol., 1970, pp. 471-481, vol. 29.

Hoyer, Patrik O., 'Non-negative Matrix Factorization with Sparseness Constraints,' Journal of Machine Learning Research, Nov. 2004, pp. 1457-1469, vol. 5.

McNally, James, G. et al., 'Three-Dimensional Imaging by Deconvolution Microscopy,' Methods, 1999, pp. 373-385, vol. 19.

Lanteri, Henri, et al., 'Penalized maximum likelihood image restoration with positivity constraints: multiplicative algorithms,' Inverse Problems, 2002, pp. 1397-1419, vol. 18.

Starck, J.L., et al., 'Deconvolution in Astronomy: A Review,' Publications of the Astronomical Society of the Pacific, Oct. 2002, pp. 1051-1069, vol. 114.

Strong, David, et al., 'Edge-preserving and scale-dependent properties of total variation regularization,' Inverse Problems, 2003, pp. S165-S187, vol. 19.

Tikhonov, A.N., 'On the stability of inverse problems,' Compte Rendus (Doklady) de l'Academie des Sciences de l'URSS, 6 pgs, 1943, vol. 39, No. 5.

* cited by examiner

CHARGED PARTICLE MICROSCOPE PROVIDING DEPTH-RESOLVED IMAGERY

This Application claims priority from U.S. Provisional App. No. 61/758,625, filed Jan. 30, 2013, and is a Continuation-in-part of U.S. application Ser. No. 13/572,449, filed Aug. 10, 2012, which claims priority from U.S. Provisional App. No. 61/620,843, filed Apr. 5, 2012, and is a Continuation-in-part U.S. application Ser. No. 13/572,206, filed Aug. 10, 2012, which claims priority from U.S. Provisional App. No. 61/522,177, filed Aug. 10, 2011, all of which are hereby incorporated by reference.

The invention relates to a method of examining a sample using a charged-particle microscope, comprising the following steps:

Mounting the sample on a sample holder;

Using a particle-optical column to direct at least one beam of particulate radiation onto a surface S of the sample, thereby producing an interaction that causes emitted radiation to emanate from the sample;

Using a detector arrangement to detect at least a portion of said emitted radiation.

The invention also relates to a charged-particle microscope in which such a method can be performed.

As used throughout this text, the ensuing terms should be interpreted consistent with the following explanation:

The term "charged particle" encompasses an electron or ion (generally a positive ion, such as a Gallium ion or Helium ion, for example, although a negative ion is also possible; the ion in question may be a charged atom or molecule). The term may also refer to a proton, for example.

The term "microscope" refers to an apparatus that is used to create a magnified image of an object, feature or component that is generally too small to be seen in satisfactory detail with the naked human eye. In addition to having an imaging functionality, such an apparatus may also have a machining functionality; for example, it may be used to locally modify a sample by removing material therefrom ("milling" or "ablation") or adding material thereto ("deposition"). Said imaging functionality and machining functionality may be provided by the same type of charged particle, or may be provided by different types of charged particle; for example, a Focused Ion Beam (FIB) microscope may employ a (focused) ion beam for machining purposes and an electron beam for imaging purposes (a so-called "dual beam" microscope, or "FIB-SEM"), or it may perform machining with a relatively high-energy ion beam and perform imaging with a relatively low-energy ion beam. On the basis of this interpretation, tools such as the following should be regarded as falling within the scope of the current invention: electron microscopes, FIB apparatus, EBID and IBID apparatus (EBID=Electron-Beam-Induced Deposition; IBID=Ion-Beam-Induced Deposition), etc.

The term "particle-optical column" refers to a collection of electrostatic and/or magnetic lenses that can be used to manipulate a charged-particle beam, serving to provide it with a certain focus or deflection, for example, and/or to mitigate one or more aberrations therein.

The term "detector arrangement" should be broadly interpreted as encompassing any detection set-up used to register (one or more types of) emitted radiation emanating from a sample. Such a detector arrangement may be unitary, or it may be compound in nature and comprise a plurality of sub-detectors, e.g. as in the case of a spatial distribution of detector units about a sample table, or a pixelated detector.

In what follows, the invention will—by way of example—often be set forth in the specific context of electron microscopes. However, such simplification is intended solely for clarity/illustrative purposes, and should not be interpreted as limiting.

Electron microscopy is a well-known technique for imaging microscopic objects.

The basic genus of electron microscope has undergone evolution into a number of well-known apparatus species, such as the Transmission Electron Microscope (TEM), Scanning Electron Microscope (SEM), and Scanning Transmission Electron Microscope (STEM), and also into various sub-species, such as so-called "dual-beam" tools (e.g. a FIB-SEM), which additionally employ a "machining" beam of ions, allowing supportive activities such as ion-beam milling or ion-beam-induced deposition, for example. In traditional electron microscopes, the imaging beam is "on" for an extended period of time during a given imaging session; however, electron microscopes are also available in which imaging occurs on the basis of a relatively short "flash" or "burst" of electrons, such an approach being of potential benefit when attempting to image moving samples or radiation-sensitive specimens, for example.

When a beam of particulate radiation (such as an electron beam or ion beam) impinges on a sample, it generally interacts with the sample in a manner that causes different types of emitted radiation to emanate from the sample. Such emitted radiation may, for example, comprise Secondary Electrons, Backscatter (BS) Electrons, visible/infrared/ultraviolet light (fluorescence and cathodoluminescence) and X-rays. Of these radiation types, electrons are relatively easy and cheap to detect, e.g. using a photo-multiplier tube (PMT) in conjunction with a scintillator [whereby it should be noted that the employed PMT may be based on an evacuated vitreous tube design with dynodes, or may instead employ a solid-state semiconductor-based detection element—e.g. as in the case of so-called Multi-Pixel Photon Counters, which are also referred to as SSPMs (Solid State Photo-Multipliers)]. The detection of visible/infrared/ultraviolet light is also relatively straightforward, and can again be performed using a PMT (without scintillator) or a photodiode cell, for example. On the other hand, X-ray detectors generally tend to be relatively expensive and slow, and typically offer a relatively limited field of view, but they are conventionally of great use in performing compositional/elemental analyses of samples, such as in the case of so-called EDS (Energy Dispersive X-ray Spectroscopy) detectors, for example.

A method as set forth in the opening paragraph is known from U.S. Pat. No. 8,232,523, which shares some inventors with the current invention. In said application, a sample is probed by a SEM electron beam at a range of different input beam energies (landing energies), and the intensity of BS electrons emanating from the sample is measured. The data thus obtained are subsequently automatically processed, by using second-order and higher-order statistics from a range of Blind Source Separation (BSS) techniques to deconvolve signals coming from different layer depths (z-levels) within the sample. In this way, one is able to calculate a set of images of the sample for a corresponding set of said different layer depths.

However, the approach in the previous paragraph has a number of significant shortcomings. For example, the described statistical BSS approach only works if it is assumed that, for an input beam of charged particles impinging on a sample, the Point Spread Function (PSF) is highly laterally confined, i.e. essentially two-dimensional along the direction of impingement; although this assumption may (approximately) hold true for certain input beam parameters and sample materials, it will not be a satisfactory assumption in a host of other practical situations (e.g. when investigating inhomogeneous samples of unknown structure). A further drawback of the known method is that, in order to construct the desired depth-resolved imagery, a series of measurements at a whole range of different landing energies must be performed; however, since adjusting the landing energy of the input particles tends to be a relatively time-consuming and cumbersome operation, this aspect of the known approach makes it relatively tedious, and can also lead to increased cumulative radiation damage to samples under investigation, particularly relatively delicate biological and mineralogical samples.

It is an object of the invention to address these issues. In particular, it is an object of the invention to provide a more generic method of performing spatially resolved imagery on a sample, in which the interaction between the imaging beam and the sample can be characterized by a more general PSF. Moreover, it is an object of the invention to provide a method in which a charged-particle microscope can be employed to acquire depth-resolved imagery from a sample without having to adjust the landing energy of the imaging beams. In particular, it is an object of the invention that such a method should lend itself to application in a SEM.

These and other objects are achieved in a method as set forth in the opening paragraph, characterized by the following steps:

Embodying the detector arrangement to detect electrons in the emitted radiation;

Recording an output $O_n$ of said detector arrangement as a function of kinetic energy $E_n$ of said electrons, thus compiling a measurement set $M=\{(O_n, E_n)\}$ for a plurality of values of $E_n$;

Using computer processing apparatus to automatically deconvolve the measurement set M and spatially resolve it into a result set $R=\{(V_k, L_k)\}$, in which a spatial variable V demonstrates a value $V_k$ at an associated discrete depth level $L_k$ referenced to the surface S, whereby n and k are members of an integer sequence, and spatial variable V represents a physical property of the sample as a function of position in its bulk.

In the context of the current invention and the terminology used herein, it should be noted that said "spatial variable" V is a three-dimensional variable or, equivalently, each of its components $V_k$ is a two-dimensional variable at a particular level $L_k$. It can represent a quantity such as contrast, intensity, density variation, atomic weight, staining concentration, electron yield, etc., all of which are directly or indirectly determined by physical characteristics of (the material of) the sample, and on the basis of which it is possible to construct an entity such as an image, map or spectrum, for example. The skilled artisan will be well able to grasp this concept.

In what follows, the invention may be explained for the specific case of BS electron detection; however, such simplification is intended solely for clarity/illustrative purposes, and should not be interpreted as limiting. The inventive approach also works for secondary electrons, although its usefulness in this case may be limited by the (generally) relatively low intrinsic production depth of secondary electrons; nevertheless, it should be remembered that secondary electrons can also be produced deeper in a material as a higher-order "knock-on" effect resulting from interaction of BS electrons with the material in question, whence it may become more interesting to be able to depth-resolve the secondary electrons thus produced.

In experiments leading to the invention, the inventors recognized that BS electrons emanating from a sample will be emitted from different depths (L) within that sample; consequently, imagery or spectroscopy (for example) based on the detection of such electrons will entail an inevitable convolution of data from these different depths. However, the inventors also realized from mathematical modeling that, although electrons emanating from a given depth generally demonstrate a distribution of energies (E), each such distribution tends to have a statistical peak at a particular energy value specific to the depth in question. Moreover, it was observed that there was a substantially monotonic linear functional dependence between said peak energy of the detected electrons and the corresponding depth from which were emitted; according to this functional dependence, emerging electrons with relatively small energies tend to be characterized by more deep-layer emission, whereas emerging electrons with relatively large energies tend to be characterized by more top-layer emission. Consequently, if a detector collects BS electrons with a particular energy value $E_n$ (e.g. with the aid of suitable filtering and/or sorting techniques—see below), then the output $O_n$ of that detector can be expressed as a sum of weighted contributions from sources at different depth levels (z-coordinates) within the sample, namely:

$$O_n(E_n) = \sum_i^n {}^n W_i f_i(L_i)$$

where the factors ${}^n W_i$ are weights and the term $f_i$ represent some function of depth $L_i$. Similarly, if a detector collects BS electrons propagating with a different energy $E_m$, then the output $O_m$ of that detector can be expressed as a similar but different sum:

$$O_m(E_m) = \sum_i^m {}^m W_i f_i(L_i)$$

where the weights ${}^m W_i$ are generally different to the weights ${}^n W_i$ because of the depth/peak-energy dependency alluded to above. The inventors examined this convoluted problem and developed a mathematical framework whereby it could be (fully automatically) deconvolved, allowing raw measurement data accumulated at different energy values to be converted into spatially resolved result data comprising information about the sample (e.g. contrast maps) as a function of different discrete depth layers below the sample surface. This technique therefore effectively performs a "depth-from-energy" conversion.

The mathematical framework developed by the inventors can be set forth as follows:

(i) When a charged-particle beam strikes a sample, it will produce a submerged zone of interaction that is characterized by a so-called Point Spread Function (PSF). This PSF describes the shape of the signal-producing volume perceived by an employed detector.

(ii) The formation of an image I in a (linear) sample can be described as a three-dimensional (3D) convolution (*) of a PSF K and a spatial variable V representing some physical property of the sample as a function of position in its bulk (e.g. staining concentration) such that:

$$I \sim K * V.$$

(iii) In accordance with what is described above, detecting different specific energy values (E) will confront the employed detector with different 3D PSF forms. For a component image $I_n$ out of a measurement series $n=[1, \ldots, N]$ obtained at different energy values $E_n$, component image formation can be described by:

$$I_n \sim K_n * V,$$

where $K_n$ is a PSF kernel. It should be noted that the quantity $I_n$ may correspond to the quantity $O_n$ referred to above, or it may be proportional thereto, e.g. a scaled version thereof. It is used here instead of $O_n$ simply so as to cast the present dissertation into a more general form.

(iv) The inventive deconvolution process consists of computationally recovering the various kernels $K_n$ along with the unknown spatial variable V. This can, for example, be done by minimizing a divergence (distance) D between the estimated unknown variables and the observed image sequence, i.e. obtaining:

$$\min D(I_n \| K_n * V).$$

(v) If one assumes no knowledge about either the sample or the PSF kernels, one obtains a 3D blind deconvolution task. On the other hand, if one can apply some constraints on the variables $K_n$ (see item (vi) below), then one need only optimize for the spatial variable V, resulting in the following simultaneous optimization tasks:

$$\min D \ (I_1 \| K_1 * V),$$
$$\ldots$$
$$\min D \ (I_N \| K_N * V),$$

which can be solved for V.

(vi) Possible constraints that can be applied to the values $K_n$ to allow the simplification alluded to in item (v) might, for example, include one or more of the following:
(a) Computational simulation of at least a set of values $K_n$;
(b) Empirical determination of at least a set of values $K_n$;
(c) Modeling of the PSF K as a parameterized function with a limited number of model parameters, on the basis of which at least a set of values $K_n$ can be estimated;
(d) Logical solution space limitation, whereby theoretically possible values $K_n$ that are judged to be physically meaningless (e.g. negative values) are discarded;
(e) Inference of a second set of values $K_n$ by applying extrapolation and/or interpolation to a first set of values $K_n$.

(vii) The minimum divergence referred to in points (iv) and (v) could, for example, be selected from techniques such as the Least Squares Distance, Csiszar-Morimoto F-divergences, Bregman Divergences, Alpha-Beta-Divergences, the Bhattacharyya Distance, the Cramér-Rao Bound, and various derivatives, hybrids and combinations of these.

As regards the constraints alluded to in item (vi), the following supplemental elucidation can be given.

In (a), mathematical techniques are used to emulate the behavior of charged particles and photons in materials, allowing the form of the PSF to be calculated and representative values $K_n$ to be predicted. The accuracy and extent of the simulation outcome will depend inter alia on the computational/computer resources dedicated to the task in question. Examples of mathematical simulation techniques suitable for this purpose are Monte Carlo methods, Finite Element Analysis, etc.

In (b), use is made of observations of the actual behavior of charged particles and photons in given materials. Such observations may, for example, be the outcome of actual imaging sessions performed on other samples, or of specific experiments performed on homogeneous material samples, etc. For example, when employing the current invention to image a semiconductor sample comprising a portion of a silicon wafer on which various patterned metallic and dielectric layers have been deposited, one might derive a collection of $K_n$-values from one or more of the following:
Other imaging sessions performed on similar semiconductor samples;
Specific "calibration tests" performed on blank silicon wafers;
Investigative experiments performed using various test coatings on silicon wafers,
etc.

In (c), one attempts to intuitively estimate what mathematical form a PSF might have, and then construct a parameterized model on this basis, using a limited number of relatively straightforward model parameters. A similar approach is used to construct, for example, climate change models, or behavioral models of crowds. By definition, the outcome of such a model will be a simplification, but it will allow a good general grasp of the basic conduct of the system being investigated.

In (d), one seeks to intuitively limit the size of a possible solution space by "weeding out" results that are theoretically possible but that are adjudged to be devoid of physical reality. For example, one might constrain the PSF to yield only positive values, or restrict it to a differential (i.e. smoothly varying) functional form, or place limits on its statistical dependence, etc.

In (e), having obtained a first set of $K_n$-values $\{K_n\}_1$, a second set of $K_n$-values $\{K_n\}_2$ is derived therefrom on the basis of extrapolation and/or interpolation. For example, if the elements of $\{K_n\}_1$ are observed to lie on a smooth, monotonic curve, one can use interpolation to infer the positions of intermediate elements and/or extrapolation to infer the positions of boundary elements of the set.

As regards the divergence alluded to in item (vii), the particular choice of the type of divergence can depend inter alia on the statistical nature of the assumed noise in the computation in question. For example, in the particular case of Gaussian noise, one could elect to minimize the Least Squares distance (also called the Mean Squares distance):

$$\min \| I_n - K_n * V \|^2,$$

whereas, for other noise models, one could use one of the other divergence measures referred to above. With regard to these broad divergence classes, the following can be noted:
Csiszar-Morimoto F-divergences (and derived measures) include the I and J Kullback-Leibler divergences, the Total Variation, Harmonic Mean, and Chi-Square measures, as well as several other entropy-based measures.
Bregman Divergences (and derived measures) include inter alia the Mahalonobis distance.
Alpha-Beta-Divergences (and derived measures) include measures such as the generalized Kullback-Leibler, Triangular Discrimination, and Arithmetic Geometric measures.
The Bhattacharyya Distance measures the similarity of two discrete or continuous probability distributions.

The actual minimization (i.e. optimization) of the chosen divergence can be performed using a variety of techniques, such as Gradient-Descent methods, Stochastic methods, and Expectation-Maximization Maximum Likelihood (EM ML) and Maximum À Posteriori (MAP) methods, for example. Iterative techniques which use derivatives, among which the Gradient Descent method, Conjugate Gradient method, Newton's method, the Quasi-Newton method, the Levenberg-Marquardt method, and Interior Point methods are some of the most commonly used; the convergence of such methods can be ensured by employing Line-Searches and Trust-Region methods, for example. As an alternative to gradient-based iterative techniques, one can employ optimization heuristics that impose fewer or no constraints on the functions to be optimized. Such heuristic methods search for solutions by relying mostly on stochastic strategies. Examples include Simulated Annealing, Evolutionary Algorithms, the Tabu Search, and Particle Swarm Optimization. Other popular heuristics include the Nelder-Mead Simplex and Hill Climbing algorithms, for example.

According to the current invention, there are different manners in which the measurement set M can be accumulated. In a specific embodiment of the invention, the employed detector arrangement is embodied to simultaneously examine a plurality of substantially discrete energy values $E_n$, such that the measurement set M is compiled by simultaneously acquiring its component data pairs $(O_n, E_n)$. In such a scenario, the employed detector arrangement is designed and implemented in such a way as to provide multiple detection modules, each module $D_n$ capable of detecting electrons with a specific energy $E_n$ (which, in practice, may be a relatively narrow energy band). In this manner, the data pairs $(O_n, E_n)$ in the measurement set M are concurrently accumulated, which can result in a shorter measurement time (and, accordingly, less radiation damage to the sample being studied). Examples of such a (parallel-measurement) set-up include the following:

(A) A suitable deflection field can be used as an energy selector, causing a beam of emergent electrons to be "fanned out" into an array of sub-beams, each sub-beam being characterized by a particular energy (band) $E_n$. Such a scenario can be regarded as a charge/energy equivalent of a mass spectrometer. The fanned-out array of beams may impinge on a corresponding array of detection modules, each of which may be a separate energy detector (such as an SSPM as alluded to above, for example) or an individual segment of a segmented detector, for example.

(B) In another possible approach, emergent electrons on their way to the detector arrangement can be caused to traverse a grid, which can be electrified with a given (repulsive) potential. Electrons with an energy below a certain threshold (determined by said potential) will not be able to get through the grid, whereas electrons with an energy above said threshold will be able to get through the grid and be detected. The grid thus acts as a high-pass filter. If desired, a "dump detector" can be employed at the entrance side of the grid, to count electrons that are turned back by the repulsive potential; in this way, both high-pass and low-pass detection can occur concurrently.

(C) In yet another scenario, use is made of a semiconductor detector in which electron-hole pairs are produced in response to capture of an electron emerging from the sample. The number of such electron-hole pairs will be proportional to the energy of the captured electron, and will determine the magnitude of a (small) measurement current whose value can be recorded. After a brief quenching time, the detector is then ready to capture a subsequent electron. Such a multi-channel detector can thus be used to sort and count captured electrons, by registering the strength of the measurement current that they produce and keeping track of the number of times that various current values are encountered.

In an alternative embodiment of the present invention, the detector arrangement is embodied to sequentially examine a plurality of substantially discrete energy values $E_n$, such that the measurement set M is compiled by sequentially acquiring its component data pairs $(O_n, E_n)$. Examples of such a (series-measurement) set-up include the following:

(D) In scenario (A) above, instead of using an array of detection modules, only one detector module (or a relatively small set of such modules) is employed. The number of available detection modules is now insufficient to view the entire fanned-out array of sub-beams in one go and, therefore, relative displacement must be used to ensure that each part of the fanned-out array is given a turn to encounter a/the detector module. This may, for example, be achieved by deflecting/displacing the fanned-out array over the detector module(s) (e.g. using suitable deflectors, or by appropriately tilting the sample holder), or by moving the detector module(s) to different parts of the fanned-out array, or some combination of both.

(E) In scenario (B) above, one can vary the employed grid potential, thus serving to adjust the pass level of the filter. Accordingly, by stepping through a series of grid potential values and performing appropriate subtraction of the electron counts registered at each such value (during a given temporal window), one can perform sequential energy resolution of the electrons offered to the grid.

The methodology set forth in the text heretofore can be described as entailing "computational slicing" into a sample. It is advantageous in that it provides very good z-resolution, but is limited as regards the extent of its z-penetration into the sample. If desired, such computational slicing can be combined with "physical slicing", so as to provide a hybrid approach that augments the obtainable z-penetration. Such physical slicing involves the physical removal of (at least one layer of) material from the sample, and may, for example, be performed using mechanical techniques (e.g. using a microtome/diamond knife) and/or radiative/ablative techniques (e.g. using a laser beam or broad ion beam, or milling the sample by scanning a focused ion beam over it) and/or etching techniques (such as beam-induced etching, chemical etching or reactive etching, for example). It should be noted that, in the case of such physical slicing, the employed layer removal procedure need not be destructive: instead, there are (mechanical) techniques that allow a removed layer to be preserved and (re-)imaged at a later juncture, if desired.

In a particular embodiment of such a hybrid computational/physical slicing approach, the above-mentioned computational slicing and physical slicing are employed alternately, whereby:

An exposed surface S of a sample is investigated using the computational slicing technique according to the current invention;

A physical slicing technique is then used to "skim" off material from the surface S, thus creating a newly exposed surface S' at a depth d below S;

This newly exposed surface S' is then investigated using the computational slicing approach according to the current invention.

If desired, several iterations of this hybrid approach can be performed, involving alternate application of computational slicing and physical slicing, and thus providing greater and greater z-penetration into the sample.

One should take care not to confuse the present invention with known tomographic techniques based on Transmission Electron Microscopy (TEM), whereby depth information is gleaned from a sample by employing a range of different sample tilt angles. Inter alia, one can identify the following differences between the two:

TEM apparatus is generally much more expensive than SEM apparatus.

The TEM approach uses much higher input beam energies (typically of the order of 200-300 keV), which can cause sample damage. In contrast, the method according to the present invention works satisfactorily with much lower input beam energies (e.g. of the order of 1-5 keV).

TEM tomography can only be used on very thin samples (generally <1 μm in thickness). Because the present invention does not rely on transmission of electrons through the sample, it does not suffer from this restriction on sample thickness.

A SEM-based application of the present invention has a much greater lateral reach than a TEM-based technique, because of the (lateral) scanning nature of the former.

By its very nature, TEM tomography does not generate the type of convoluted depth data associated with the present invention, and, accordingly, does not require statistical processing techniques to perform depth resolution upon such convoluted data.

Care should be taken not to confuse the very broad and general methodology of the current invention with the much more restricted techniques set forth in various prior-art publications. In this respect, it is important to explicitly note that:

The approach of the current invention does not place any ab initio restrictions on the form/nature of the employed PSF; it instead allows a completely general, spatially three-dimensional PSF to start off with.

The approach of the current invention does not place any ab initio restrictions on the substance/nature/structure of the material in the sample being investigated; it instead permits a completely general bulk sample to be assumed.

The present invention places no ab initio restrictions on the type/geometry of radiation used to perform the various measurement sessions.

The current invention performs a series of different measurement sessions at different emergent electron energy values, thereby accruing a convoluted mass of data from different (three-dimensional) positions within a sample. This mass of data is then subjected to automatic deconvolution so as to "un-mix" the data mass into individually resolved contributions from distinct voxels within the sample. In this way, volume re-construction of the sample is achieved, thus revealing details from different depths (z) and from different lateral positions (x, y).

The inventive deconvolution procedure iterates over all PSFs during said re-construction process. In this regard, the PSFs are deconvolved in a coupled/concurrent fashion rather than in an independent fashion. Such coupling tends to enhance convergence to a good solution set. To better understand the difference between coupled/concurrent and uncoupled/separated deconvolution, one can make an analogy to a problem in which simultaneous equations are solved. If the equations are indeed solved simultaneously (i.e. in a coupled manner), then all variables in the equations remain "floating" during the (various iterations of the) solving process. On the other hand, if the equations are tackled one-at-a-time (i.e. in an uncoupled manner), then all variables except one will have to be "pinned" during the solving process for each individual equation, leading to a much more restricted solution set.

To highlight these aspects of the current invention, some important distinctions can be pointed out with reference to two particular journal articles, namely:

D1: H. Niedrig, E. I. Rau, *Information depth and spatial resolution in BSE microtomography in SEM*, Nuclear Instruments and Methods in Physics Research B 142 (1998), pp. 523-534;

D2: A. V. Gostev et al., *Information depth of the backreflected electron mode in scanning electron microscopy*, Bulletin of the Russian Academy of Sciences—Physics 62(3) (1998), pp. 475-480.

Both of these articles study a sample with a very specific, simplistic structure, comprising a sandwich of three stacked, homogeneous layers. Spectral measurement results are described using a model of three simultaneous equations whose coefficients are determined on the basis of the physics of electron interaction in the sample. These coefficients are initially calculated using Monte Carlo simulations, and then adjusted manually by an operator. See, for example:

D1: p 528, left column, half way: "Initially $k_{ij}$ is chosen by the Monte-Carlo method and then it is chosen with more precision by the operator in the visual way".

D2: p 477, left column, after equations (4): "These parameters are initially estimated by the Monte Carlo method and then, more precisely, visually by an operator".

The need for such manual adjustment is not surprising in view of the simplistic model used by the authors of D1 and D2, and the non-coupled manner in which they determine the coefficients that they use. In contrast to the technique of the current invention, the approach in D1 and D2 is non-iterative, in that coefficients—once they have been calculated—are not re-submitted in a subsequent iterative cycle so as to undergo further refinement; instead, a single iteration is calculated and then some form of manual adjustment has to be performed in an attempt to "touch up" the shortcomings of the result. This aspect of D1 and D2 reveals why they use such a simplistic sample structure and model: it's bad enough trying to manually adjust nine different coefficients in the employed set of three simultaneous equations, not to mind what would be necessary for a more complex sample (e.g. twenty five coefficients for a five-layer sample). It also explains why the employed model in D1 and D2 is essentially a one-dimensional simplification that is basically only concerned with layer contributions in a direction normal to the sample: if one were to attempt to include possible contributions from lateral and diagonal components, the solution in D1 and D2 would become unworkable. So, the non-automatic approach in D1 and D2 does not offer a means of addressing a beam/sample interaction involving a full 3-dimensional PSF. That is why the aim of D1 and D2 is to inspect interface layers for defects, rather than to perform the full-blown reconstruction of the current invention.

Many of the mathematical techniques in the current document are also discussed in European Patent Application EP12163262, where they are presented in the context of a different (but nevertheless somewhat related) problem. That latter document is incorporated herein by reference.

BRIEF DESCRIPTION OF THE DRAWINGS

The invention will now be elucidated in more detail on the basis of exemplary embodiments and the accompanying schematic drawings, in which.

In the Figures, where pertinent, corresponding parts are indicated using corresponding reference symbols.

EMBODIMENT 1

Figure 1A:
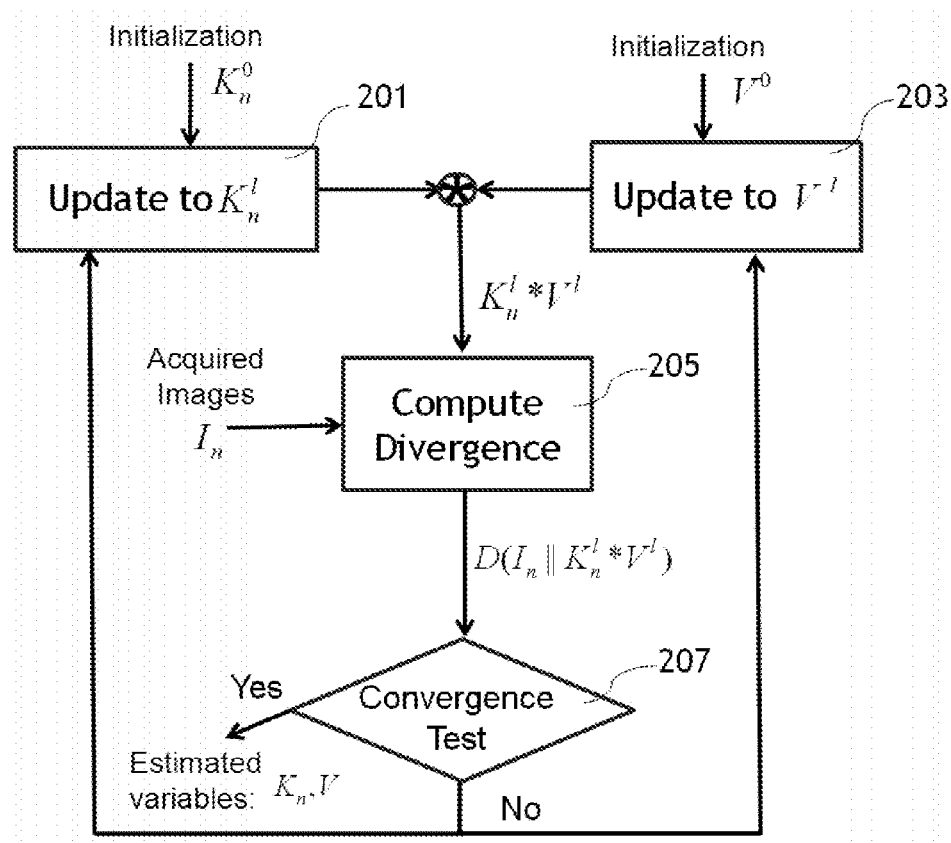
FIGS. 1A and 1B are mutually associated flowcharts that depict a general scheme for performing the method according to the present invention.
Figure 1B:
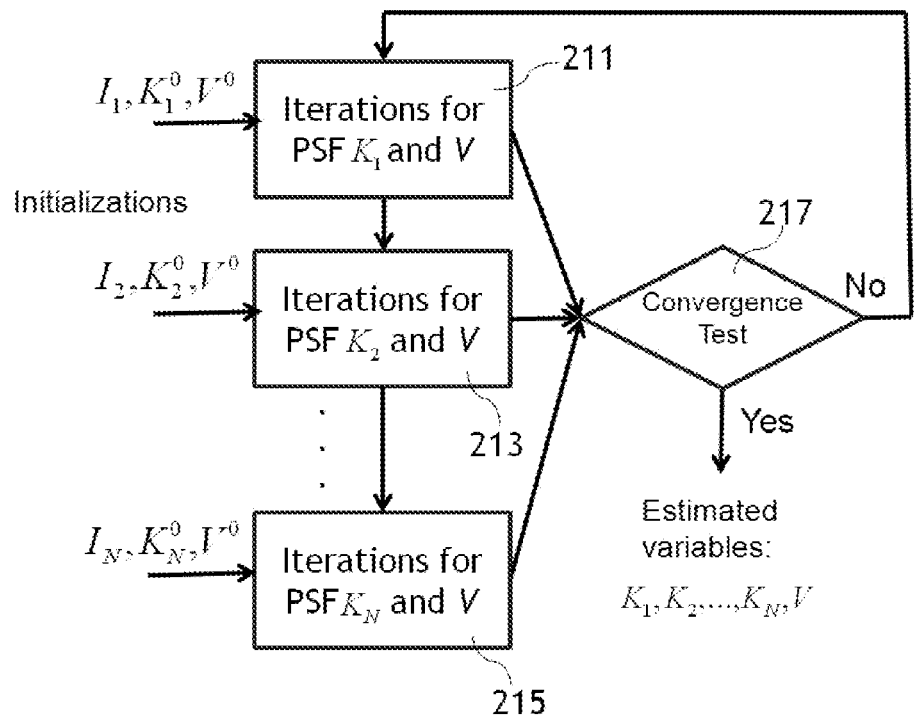

FIGS. 1A and 1B are mutually associated flowcharts that depict a general scheme for performing the method according to the present invention. With reference to the nomenclature introduced in the discussion above, it is noted that:

FIG. 1A depicts an algorithm for a given PSF kernel $K_n$ at iteration l. Multiple iteration cycles for a given $K_n$ are applied sequentially.

The iterative scheme in FIG. 1A can be sequentially applied to each PSF and to the spatial variable V. For any pair $K_n$, V, one can have one or more iterations at each cycle.

In the depicted flowcharts, the indicated steps will now be elucidated in more detail. Starting with FIG. 1A:

201: This step represents the value of $K_n$ at iteration l (i.e. $K_n^l$). In the special case l=1, a preceding initialization procedure will have been performed, so as to "kick start" the iteration procedure.

203: Similarly, this step represents the value of V at iteration l (i.e. $V^l$). Once again, in the special case l=1, a preceding "kick start" initialization procedure will have been performed.

205: The convolution $K_n^l * V^l$ is calculated using the output of steps 201 and 203. One now introduces a quantity $I_n$ that is a dimensionless/scaled version of the quantity $O_n$. For example, if $O_n$ is measured in volts, its numerical value in volts is dimensionless, and can, if desired, be scaled by the value of the fundamental electron charge (e) so as to effect a conversion to a numerical value in electron-volts (eV), for example. This is purely a matter of choice in any given situation, as will be readily grasped by the skilled artisan. The quantity $I_n$ will be referred to hereinafter as an "image". In step 205, a divergence between image $I_n$ and the convolution $K_n^l * V^l$ is determined, i.e. D $(I_n \| K_n^l * V^l)$ is calculated.

207: Here, it is determined if the divergence calculated in step 205 is minimal, i.e. if convergence has been attained. If it is ("Yes"), then one has distilled the sought values $K_n$ and V; if it is not ("No"), then one returns to the top of the flowchart for the next iteration (l+1).

Turning now to FIG. 1B, this figure represents a generalization of FIG. 1A. Instead of just showing the procedure for only one element n of the measurement sequence [1, . . . , N], it now depicts all the elements 1 . . . N in this sequence:

211, 213, 215: Each of these steps corresponds to the cumulative steps 201, 203 and 205 of FIG. 1A, but now shown for the individual cases n=1 (211), n=2 (213) and n=N (215).

217: This step corresponds to step 207 of FIG. 1A.

For a specific example as to how the minimum divergence problem set forth above can be formulated and solved, reference is made to the next Embodiment below.

EMBODIMENT 2

One intuitive way to consider the variable-kernel deconvolution task at hand is to formulate it using so-called Bayesian statistics.

One first defines a number of probabilities that will be used throughout the elucidation below:

$Pr(V|I_n)$ is the probability of distilling the spatial variable V, given the acquired input values $I_n$ (see the above discussion of step 205 in the flowchart of FIG. 1A for an explanation of the concept of "image" value $I_n$). Similarly, $Pr(I_n|V)$ is the probability of observing the image values $I_n$ given a sample structure described by V.

$Pr(V)$ is the so-called prior probability associated with V, representing one's knowledge about the structure to be reconstructed.

$Pr(I_n)$ is the probability associated with the acquired images; however, this is essentially a constant, given that the images $I_n$ are actually observed/measured values.

Using Bayes' rule one now obtains:

$$Pr(V \mid I_n) = \frac{Pr(I_n \mid V) Pr(V)}{Pr(I_n)} \tag{1}$$

In the Bayesian framework, the current problem can be expressed as the following maximization task:

$$\hat{V} = \mathrm{argmax}_{V \geq 0} \{Pr(V|I_n)\}, \tag{2}$$

in which one needs to enforce the positivity of the reconstructed variable V. This is necessary in order to obtain a physically meaningful solution. More commonly, one will use the so called log-likelihood function to simplify the calculations:

$$\hat{V} = \mathrm{argmin}_{V \geq 0} \{-\log(Pr(V|I_n))\} \tag{3}$$

Concretely, the current imaging process is well represented by a Poisson process. Given the nature of charged-particle and X-ray detectors, one can assume that, at each voxel x in a 3D grid $\Omega$, the image is formed by the realization of independent Poisson processes. This leads to:

$$Pr(I_n \mid V) = \Pi_{x \in \Omega} \frac{((K_n * V)(x))^{I_n(x)} \exp(-(K_n * V)(x))}{I_n(x)!}, \tag{4}$$

wherein it should be noted that "x" is not the linear Cartesian coordinate x, but is instead an algebraic denotation of a three-dimensional position.

To recover the volume V, one needs to minimize the criterion:

$$J((I_n \mid V)) = -\log (Pr(I_n \mid V)) \tag{5}$$
$$= \Sigma_{x \in \Omega}((K_n * V)(x)) - I_n(x).\log((K_n * V)(x)) + \log(I_n(x)!)$$

Given that the $\Sigma_{x \in \Omega} \log(I_n(x)!)$ term does not contain any variables, the criterion can be redefined as:

$$J((I_n|V)) = \Sigma_{x \in \Omega}((K_n * V)(x)) - I_n(x) \cdot \log((K_n * V)(x)) \tag{6}$$

It is important to note that this criterion is related to Kullback-Leibler generalized I-divergence $IDIV(I_n\|V)$. This can be seen from the definition of I-divergence:

$$IDIV(I_n \| V) \stackrel{def}{=} \Sigma_{x \in \Omega} I_n(x) \log\left(\frac{I_n(x)}{(K_n * V)(x)}\right) - \Sigma_{x \in \Omega} I_n(x) - (K_n * V)(x)) \tag{7}$$

from which one can obtain:

$$IDIV(I_n\|V) = J(I_n|V) - \Sigma_{x \in \Omega} I_n(x) \cdot \log(I_n(x)) \tag{8}$$

The second term in (8) is a constant with regard to minimization and, hence, minimizing $J((I_n|V))$ is equivalent to minimizing $IDIV(I_n\|V)$.

Reference is now made to the following journal article:
[1] H. Lantéri, M. Roche, C. Aime, "*Penalized maximum likelihood image restoration with positivity constraints: multiplicative algorithms, Inverse Problems,*" vol. 18, pp. 1397-1419, 2002,
in which it was shown that a positivity-constrained minimization problem of the type (2) above can be solved using the following iterative scheme:

$$V^{l+1}(x) = V^l(x) \cdot \left( \frac{I_n(x)}{(K_n * V^l)(x)} * K_n(-x) \right) \quad (9)$$

This algorithm is also known as the Maximum-Likelihood Expectation Maximization algorithm, which is further described, for example, in the following references:
[2] L. Shepp, Y. Vardi, "*Maximum-Likelihood reconstruction for emission tomography,*" IEEE Transactions on Medical Imaging, MI-5, pp. 16-22, 1982.
Richardson, William Hadley. "*Bayesian-Based Iterative Method of Image Restoration*", JOSA 62 (1), pp 55-59, 1972.

Convergence in expression (9) can be accelerated by using the exponent q as follows:

$$V^{l+1}(x) = V^l(x) \cdot \left( \frac{I_n(x)}{(K_n * V^l)(x)} * K_n(-x) \right)^q \quad (10)$$

Typically, $q \in [1, 1.5]$ and, in addition to acceleration, it can act as a regularizing factor. In the current case, the iterative algorithm needs to be sequentially used for all kernels $K_n$ associated with the different PSFs. Convergence can be assessed empirically or based on other criteria, such as the relative change in the variables.

If one needs to recover or adjust the values of the PSF kernels $K_n$, one can use alternate minimization of the spatial variable V and the $K_n$ variables. One then obtains the following algorithm:

$$V^{l+1}(x) = V^l(x) \cdot \left( \frac{I_n(x)}{(K_n^l * V^l)(x)} * K_n^l(-x) \right)^q \quad (11)$$

$$K_n^{l+1}(x) = K_n^l(x) \cdot \left( \frac{I_n(x)}{(K_n^l * V^{l+1})(x)} * V^{l+1}(-x) \right)^q$$

One can choose to have more iterations for the kernels $K_n$ or for the spatial variable V at each cycle; such a choice can be determined based on experience/experimentation. For example, it is generally noticed that V tends to converge faster, and hence more iterations can be spent searching for the different values $K_n$.

If prior knowledge about the PSF or V is available, it can be incorporated into the Bayesian formulation using a combination of conditional Pr(.|.) and joint probabilities Pr(.,.) as follows:

$$Pr(V, K_n | I_n) = \frac{Pr(I_n | V, K_n) Pr(V) Pr(K_n)}{Pr(I_n)} \quad (12)$$

It follows that the minimization problem (2) is then modified as follows:

$$\hat{V} = \mathrm{argmax}_{V \geq 0} \{Pr(V, K_n | I_n)\} \quad (13)$$

and the log-likelihood criterion to be minimized then becomes $$J(V, K_n | I_n) = -\log(Pr(I_n | V, K_n)) - \log(Pr(V)) - \quad (14)$$

$$\log(Pr(K_n))$$

$$= J(I_n | V, K_n) + J(V) + J(K_n)$$

While the first term is the data term that ensures that one fits the observations, the second and third terms are known as regularization terms that use one's knowledge and assumptions about the variables to limit the space of solutions and reduce the effects of noise. The criterion $J(V, K_n | I_n)$ can be minimized using the Maximum Likelihood Expectation Maximization approach. Optimization can be also carried out using a variety of other convex and non-convex methods, as set forth, for example, in the following reference:
[4] William H. Press, Saul A. Teukolsky, William T. Vetterling, Brian P. Flannery, *Numerical Recipes in C: The Art of Scientific Computing*, Second Edition (1992).

For completeness, it is noted that the approach set out in the current Embodiment can be regarded as a hybrid/variant of the so-called Richardson-Lucey Algorithm (RLA). The RLA is a known mathematical technique that can be applied to solve a variety of problems. For example, it was used by NASA scientists in an attempt to computationally improve blurred imagery from the original (i.e. uncorrected) Hubble Space Telescope.

EMBODIMENT 3

The prior distributions of the sample structure [Pr (V)] and the PSF [Pr ($K_n$)] can play an important role of regularization in the process of maximizing the so-called posterior probability Pr(V, $K_n | I_n$). Several well-known regularization methods are set forth in the following publications.
[5] A. N. Tikhonov, *On the Stability of Inverse Problems*, Proceedings of Doklady Akademii Nauk SSSR, Russian Academy of Sciences, 1943, pp. 195-198.
[6] D. Strong, T. Chan, *Edge-preserving and scale-dependent properties of total variation regularization*, Inverse Problems, 2003, 19: S165-S187.
[7] P. O. Hoyer, *Non-negative Matrix Factorization with Sparseness Constraints*, Journal of Machine Learning Research 5, 2004, pp. 1457-1469.
[8] W D. Dong, H J. Feng, Z. H. Xu, Q. Li, *A piecewise local regularized Richardson-Lucy algorithm for remote sensing image deconvolution*, Optics and Laser Technology 43, 2011, pp. 926-933.

Known regularization methods include Tikhonov regularization [5], Total Variation (TV) regularization [6], sparse prior regularization [7], piecewise local regularization [8], etc.

For the popular TV regularization, a regularization term J(V) is defined by the integration of absolute gradients of the sample structure V, as follows:

$$J(V) = -\log(Pr(V)) = \lambda \cdot \sum_x |\nabla V(x)|$$

The total function to be minimized is then:

$$J(V|I_n) = J(I_n|V) + J(V)$$

$$= \sum_{x \in \Omega} ((K_n * V)(x)) - I_n(x) \cdot \log((K_n * V)(x)) +$$

$$\lambda \cdot \sum_x |\nabla V(x)|$$

The derivative of J(V) with respect to V is $$\frac{\partial}{\partial V} J(V(x)) = -\lambda \cdot div\left(\frac{\nabla V(x)}{|\nabla V(x)|}\right),$$

where "div" stands for divergence in the context of vector calculus (as opposed to divergence in the context of statistical distance). One minimizes $J(V|I_n)$ by setting the derivative of $J(V|I_n)$ to be zero, with $\Sigma_x K_n(x)=1$, which results in the following iterative scheme:

$$V^{l+1}(x) = \frac{V^l(x)}{1 - \lambda \cdot div\left(\frac{\nabla V}{|\nabla V|}\right)} \cdot \left(\frac{I_n(x)}{(K_n * V^l)(x)} * K_n(-x)\right)$$

where λ effectively controls the weight of TV regularization during the optimization. The main advantage of TV as a regularization method is that it preserves the edges in the resulting image while reducing noise in homogeneous regions.

EMBODIMENT 4

As an alternative to the mathematics presented above, the following deconvolution methods also deserve mention in the context of the present invention.
(I) Maximum Entropy Methods The Maximum Entropy (ME) method has been widely used with success for many years and is, for example, one of the practical choices in radio astronomy for image restoration applications. In contrast to the Maximum Likelihood (ML) approach, which aims to maximize a probability function, the general approach of ME reconstruction is to maximize an entropy function subject to constraints on the image estimation:

$$\hat{V} = \operatorname{argmax}\{Ent(V)\}$$

such that $I_n = K_n * V$
where "Ent" represents the entropy function. The idea behind the ME method is to find the solution that is not only compatible with the image formation process but that also has the highest information content.

The most popular entropy function in image restoration is the Shannon entropy, defined directly on the gray-levels of the image as:

$$Ent(V(x)) = \sum_x V(x) \cdot \log V(x)$$

which has its origin in information theory. Another entropy function found in the literature is the Burg entropy:

$$Ent(V(x)) = \sum_x \log V(x)$$

The ME problem can, for example, be solved as a deterministic constrained convex optimization problem using the Multiplicative Algebraic Reconstruction Technique (MART), which minimizes the negative Shannon entropy function via an iterative scheme. The MART technique involves a multiplicative correction to the voxel intensity based on the ratio of the recorded pixel intensity $I_n(j)$ and the projection of voxel intensities $(K_n * V^l)(j)$ from the previous iteration:

$$V^{l+1}(j) = V^l(j)\left(\frac{I_n(i)}{(K_n * V^l)(i)}\right)^{wK_n(i,j)}$$

where w is a relaxation parameter that controls the step size, $V^l(j)$ is the $j^{th}$ element of the $l^{th}$ iteration on V, and $K_n(i,j)$ is the i, $j^{th}$ element of $K_n$. Each voxel's intensity is corrected by one projection at a time, which means a single iteration is completed only after every projection has been considered.

For more information on MART, reference is to made to:
[9] R. Gordon, R. Bender, and G. T. Herman, *Algebraic reconstruction techniques for three-dimensional electron microscopy and x-ray photography*, J. Theoretical Biology 29, 1970, pp 471-481.
(II) Linear Methods For an image formation model applied without further assumptions on noise statistics, the estimate for the sample structure is given by:

$$V = F^{-1}\left(\frac{F(I_n)}{F(K_n)}\right)$$

where F and $F^{-1}$ denote Fourier and inverse Fourier transforms, respectively. Because $K_n$ is band-limited, the denominator of this expression is close to zero at many frequencies, and the direct deconvolution tends to suffer from severe noise amplification. One way to tackle this problem is by using a truncated inverse filter (see reference [10] below):

$$V = \begin{cases} F^{-1}\left(\frac{F(I_n)}{F(K_n)}\right) & \text{if } |F(K_n)| \geq \varepsilon \\ 0 & \text{else} \end{cases}$$

where ∈ is a small positive constant. The solution is generally ill-posed, and a regularization term can be introduced to find a stable solution. For example, Tikhonov regularization consists of minimizing the term:

$$J(V) = \|I_n - K_n * V\| + \lambda \|H * V\|$$

where H denotes a high-pass filter. The solution is obtained in the Fourier space (see reference [11] below):

$$V = F^{-1}\left(\frac{F(K_n)F(I_n)}{|F(K_n)|^2 + \lambda \cdot |F(H)|^2}\right)$$

where λ is the regularization parameter, representing the trade-off between fidelity to the data and smoothness of the restored image.

For more information on the linear methods discussed here, reference is made to the following publications:
[10] J. G. McNally, T. Karpova, J. Cooper, J. A. Conchello, *Three-dimensional imaging by deconvolution microscopy*, Methods, vol. 19, no. 3, pp. 373-385 (1999).
[11] J. L. Starck, E. Pantin, *Deconvolution in Astronomy: A Review*, Astronomical Society of the Pacific, 114: 1051-1069 (2002).

It should be noted that linear methods as set forth here do not restore the sample structure's frequency components beyond the PSF bandwidth. In addition, these methods can give negative intensity in the estimated image, and tend to be very sensitive to errors in the PSF used for the estimation, resulting in artifacts.

One may, if desired, combine different types of the methods listed here for the complete deconvolution problem involved. For example, one could first use a Maximum À Posteriori (MAP) or ML method to estimate the PSF, and then use the linear or ME approach to deconvolve the sample structure.

EMBODIMENT 5

Figure 2:
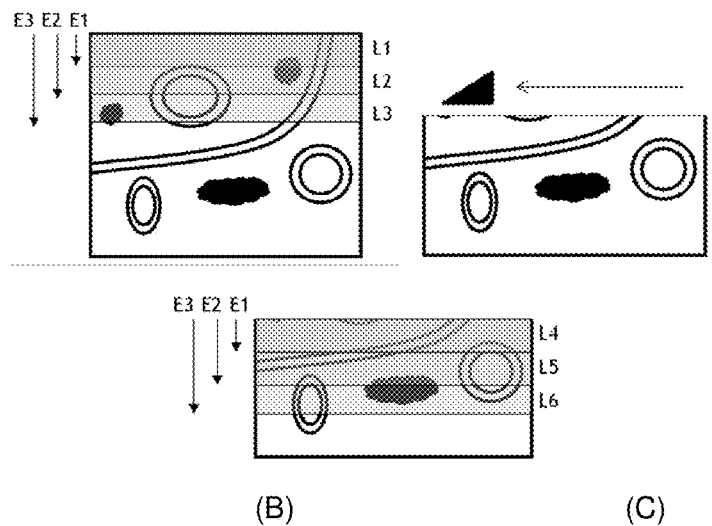
FIG. 2 illustrates a hybrid technique involving the alternate use of computational slicing and physical slicing in accordance with an embodiment of the current invention.

FIG. 2 illustrates (in a stylized manner) an embodiment of the current invention whereby computational slicing is combined with physical slicing, so as to allow charged-particle-microscopy-based 3D volume imaging of a sample to relatively increased depths.

FIG. 2A (left) depicts a computational slicing step, whereby a sample is observed at varying emergent electron energies ($E_1$, $E_2$, $E_3$) and a 3D deconvolution algorithm is applied, as set forth above. This allows sub-surface virtual imaging of the sample to increasing penetration depths, here schematically labeled as ($L_1$, $L_2$, $L_3$).

In FIG. 2B (center), subsequent use is made of a physical slicing step, whereby a mechanical cutting device (e.g. a diamond knife) or a non-mechanical approach (e.g. involving a focused/broad beam of ions, or a focused electromagnetic beam) is used to physically "skim off" a certain depth of material from the sample, thus producing a newly exposed surface.

In FIG. 2C (right), one executes a subsequent computational slicing operation on said newly exposed surface. This allows sub-surface virtual imaging of the sample to new penetration depths, here schematically labeled as ($L_4$, $L_5$, $L_6$).

EMBODIMENT 6

Figure 3:
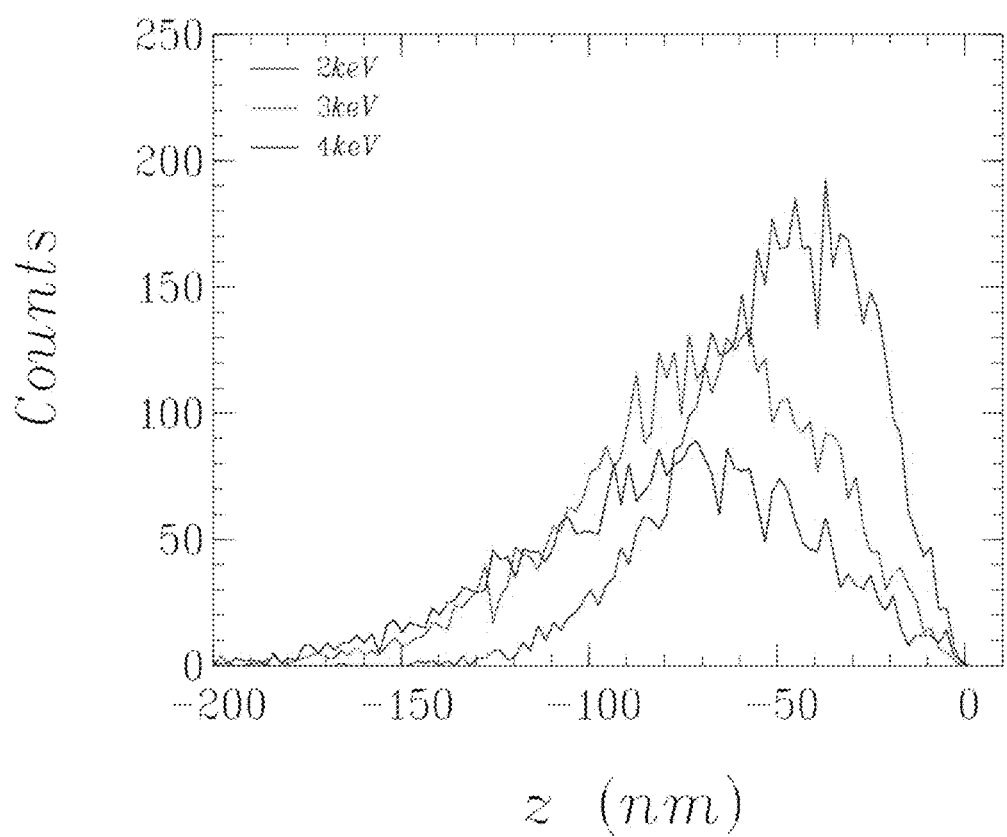
FIG. 3 shows simulation results pertaining to emission of BS electrons from a sample in a SEM, illustrating numbers of BS electrons emanating from different depths within the sample for different BS electron energy values.

FIG. 3 shows simulation results pertaining to emission of BS electrons from a sample in a SEM, illustrating numbers of BS electrons emanating from different depths within the sample for different BS electron energy values. The results come from Monte Carlo simulations, and pertain to a Si target irradiated with a 5 kV incident electron beam and a fictive BS electron detector observing along an altitude angle of 90-180 degrees with respect to the incoming beam (thus relating to any BS electron with a velocity component anti-parallel to the incident beam). The graph depicts BS electron counts as a function of production depth (in nm) for non-overlapping energy bands (of width 500 eV) centered on three different BS energy values, viz. (from right to left) 4 keV, 3 keV and 2 keV.

The Figure demonstrates that BS electrons of a given energy $E_n$ can be produced from a whole range of different depths, but that peak numbers are produced from a certain preferential depth for each value of $E_n$. More specifically, in the depicted graph:
4 keV electrons show a peak in numbers corresponding to a depth of about 40 nm;
3 keV electrons show a peak in numbers corresponding to a depth of about 65 nm;
2 keV electrons show a peak in numbers corresponding to a depth of about 75 nm.

It should be noted that these energy values are the kinetic energies of the electrons as they emerge from the sample surface, rather than their intrinsic kinetic energy upon production; it is thus logical that electrons from deeper layers should—on average—have less energy when they emerge from the sample, since they will generally have undergone greater losses in trying to escape from the sample.

EMBODIMENT 7

Figure 4:
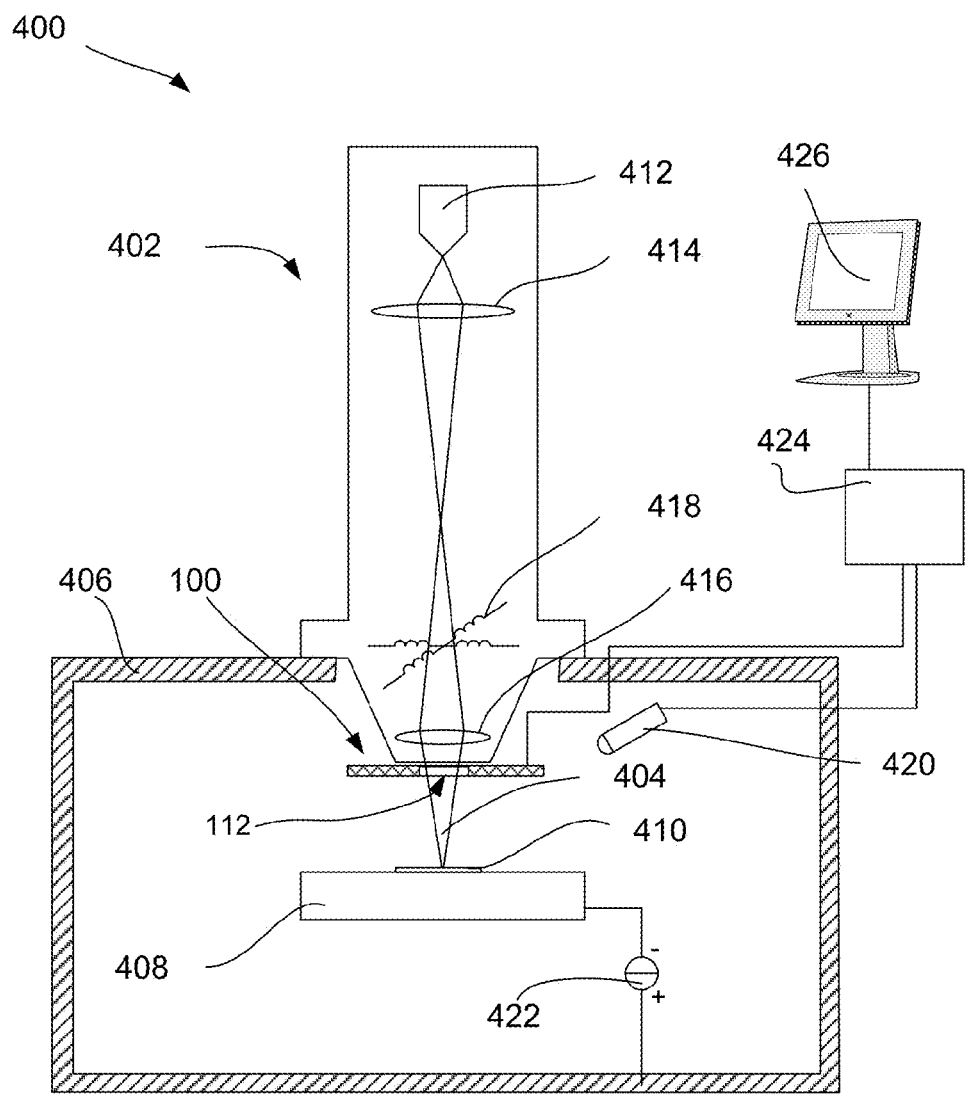
FIG. 4 renders a longitudinal cross-sectional view of aspects of a particle-optical microscope (in this case a SEM) with which the method according to the current invention can be implemented.

FIG. 4 is a highly schematic depiction of a charged-particle microscope 400, which, in this case, is a SEM. The microscope 400 comprises a particle-optical column 402, which produces a charged-particle beam 404 (in this case, an electron beam). The particle-optical column 402 is mounted on a vacuum chamber 406, which comprising a sample holder/stage 408 for holding a sample 410. The vacuum chamber 406 is evacuated using vacuum pumps (not depicted). With the aid of voltage source 422, the sample holder 408, or at least the sample 410, may be biased (floated) to an electrical potential with respect to ground.

The particle-optical column 402 comprises an electron source 412, lenses 414, 416 to focus the electron beam 404 onto the sample 410, and a deflection unit 418. The apparatus further comprises a computer processing apparatus (controller) 424 for controlling inter alia the deflection unit 418, lenses 414, and detectors 100, 420, and displaying information gathered from the detectors 100, 420 on a display unit 426.

The detectors 420, 100 are chosen from a variety of possible detector types that can be used to examine different types of radiation in different manners. In the apparatus depicted here, the following detector choices have been made:

Detector 100 is a segmented electron detector. Such a detector can, for example, be used to investigate the angular dependence of electrons emerging from the sample 410. A detector of this type is, for example, elucidated in more detail in the aforementioned European Patent Application EP12163262.

Detector 420 is used in the context of the current invention to perform energy-filtered detection of electrons emanating from the sample 410. In the present instance, the detector 420 can, for example, be a multi-channel solid-state detector of the type (C) alluded to above. Alternatively, it may be of the type (A) referred to above, and employ a deflecting field in a cavity in order to "fan out" an incoming beam of electrons into energy-sorted sub-beams than then land on an array of detection modules. Regardless of its internal workings, signals from this detector 420 serve as the basis for compiling a measurement set $M=\{(O_n, E_n)\}$ as discussed above, since the detector 420 provides output values $O_n$ that are associated with discrete electron energy values $E_n$ emanating from the sample 410.

As here rendered, both detectors 100 and 420 are used to examine electrons; however, this is purely a design/implementation choice and, if desired, one could also elect to detect other types of stimulated radiation (e.g. X-rays) in addition to electrons.

By scanning the beam 404 over the sample 410, stimulated radiation—comprising, for example, X-rays, infrared/visible/ultraviolet light, secondary electrons and backscatter (BS) electrons—emanates from the sample 410. As the emitted radiation is position-sensitive (due to said scanning motion), the information obtained from the detectors 100, 420, will also be position-dependent.

The signals from the detectors 100, 420 are processed by the processing apparatus 424, and displayed on display unit 426. Such processing may include operations such as combining, integrating, subtracting, false colouring, edge enhancing, and other processing known to the skilled artisan. In addition, automated recognition processes (e.g. as used for particle analysis) may be included in such processing. In the context of the current invention, the processing apparatus 424—and/or a dedicated separate processing unit (not shown)—can be used to perform the prescribed mathematical manipulations on said measurement set M so as to deconvolve it and spatially resolve it into the result set R discussed above.

It should be noted that many refinements and alternatives of such a set-up will be known to the skilled artisan, including, but not limited to:

The use of dual beams—for example an electron beam 404 for imaging and an ion beam for machining (or, in some cases, imaging) the sample 410;

The use of a controlled environment at the sample 410—for example, maintaining a pressure of several mbar (as used in a so-called Environmental SEM) or by admitting gases, such as etching or precursor gases;

etc.

EMBODIMENT 8

Figure 5:
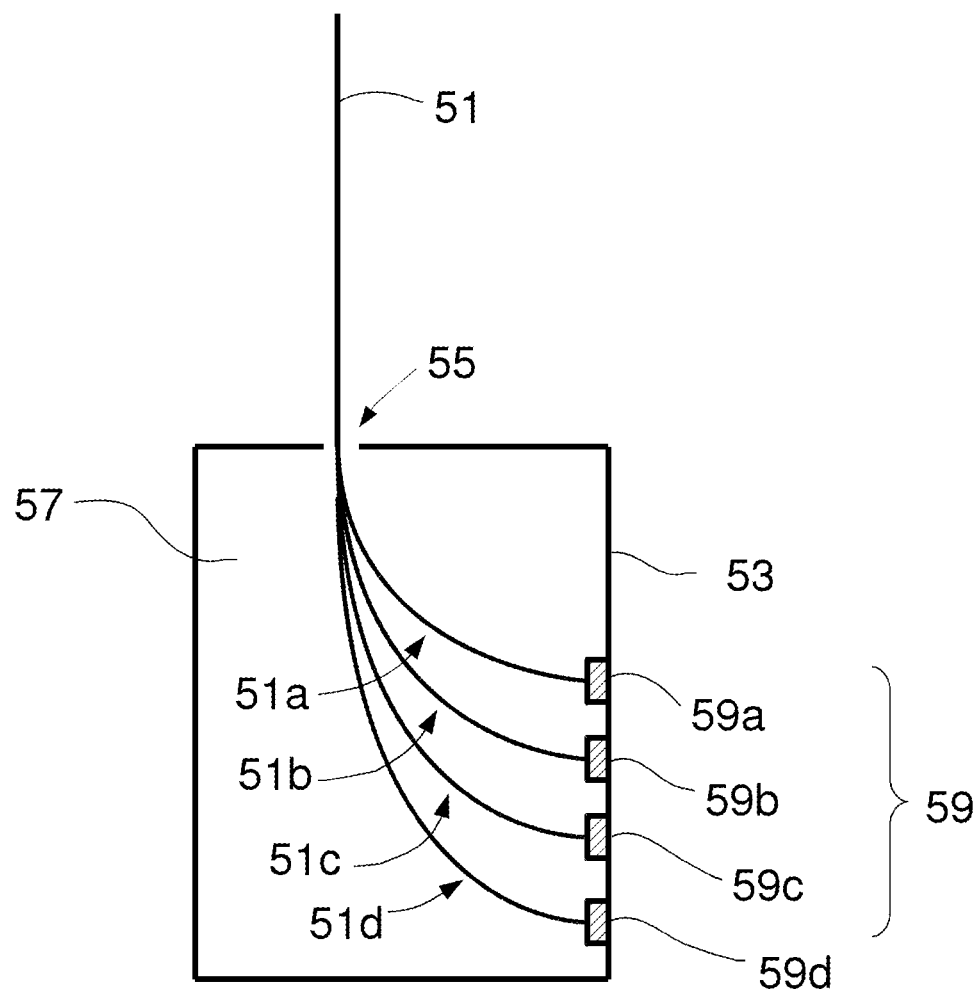
FIG. 5 illustrates the operating principle of a particular detector arrangement that can be used to produce energy-filtered outputs $O_n$ for a detected beam of electrons of mixed energies $E_n$, thus serving to compile a measurement set $M=\{(O_n, E_n)\}$ as set forth in the current invention.

FIG. 5 illustrates the operating principle of a particular detector arrangement that can be used to produce energy-filtered outputs $O_n$ for a detected beam of electrons of mixed energies $E_n$, thus serving to compile a measurement set M={$(O_n, E_n)$} as set forth in the current invention. More particularly, the depicted detector arrangement is of the type (A) set forth above.

In the Figure, a beam 51 of electrons (e.g. BS electrons) enters a measurement cavity 53 through an aperture 55. The beam 51 comprises a portion of the emitted radiation emanating from a sample (such as item 410 in FIG. 4) when it is irradiated by a beam of charged-particle radiation (such as item 404 in FIG. 4), and can, for example, be produced by causing said emitted radiation to pass through an aperture plate (not depicted). In FIG. 5, the beam 51 is depicted as being vertical but, in general, it can also have another orientation.

The interior 57 of the cavity 53 is permeated by a suitable deflecting field (not depicted), e.g. a (uniform) magnetic field with field lines perpendicular to the plane of the Figure. When they encounter this field, electrons in the beam 51 undergo a deflection, whose magnitude will depend on the kinetic energy of the electrons in question. As a result, what enters the cavity 53 as a well-defined beam 51 is converted into a fanned-out array of sub-beams—four of which (51a, 51b, 51c, 51d) are illustrated here—whereby relatively low-energy electrons in the beam 51 undergo relatively large deflections, and vice versa. These sub-beams 51a, 51b, 51c, 51d impinge upon respective detection modules 59a, 59b, 59c, 59d of detector arrangement 59, each of which modules 59a, 59b, 59c, 59d may be a separate energy detector (such as an SSPM) or an individual segment of a segmented detector, for example. Since the sub-beams 51a, 51b, 51c, 51d will each be characterized by a different electron energy $E_n$ (in practice, a relatively narrow band of energies), the detection modules 59a, 59b, 59c, 59d of the detector arrangement 59 will produce an energy-resolved output, allowing an output value $O_n$ to be assigned to each energy value $E_n$.

We claim as follows:

1. A method of examining a sample using a charged-particle microscope, comprising:
    mounting the sample on a sample holder;
    using a particle-optical column to direct at least one beam of particulate radiation onto a surface S of the sample, thereby producing an interaction that causes emitted radiation to emanate from the sample; and
    using a detector arrangement to detect at least a portion of said emitted radiation, characterized by the following steps:
        embodying the detector arrangement to detect electrons in the emitted radiation;
        recording an output $O_n$ of said detector arrangement as a function of kinetic energy $E_n$ of said electrons, thus compiling a measurement set M={$(O_n, E_n)$} for a plurality of values of $E_n$; and
        using computer processing apparatus to automatically deconvolve the measurement set M and spatially resolve it into a result set R={$(V_k, L_k)$}, in which a spatial variable V demonstrates a value $V_k$ at an associated discrete depth level $L_k$ referenced to the surface S,
    whereby n and k are members of an integer sequence, and spatial variable V represents a physical property of the sample as a function of position in its bulk.

2. The method of claim 1, wherein said detector arrangement is embodied to simultaneously examine a plurality of substantially discrete energy values $E_n$, such that the measurement set M is compiled by simultaneously acquiring its component data pairs $(O_n, E_n)$.

3. The method of claim 1, wherein said detector arrangement is embodied to sequentially examine a plurality of substantially discrete energy values $E_n$, such that the measurement set M is compiled by sequentially acquiring its component data pairs $(O_n, E_n)$.

4. The method of claim 1, wherein said detector arrangement comprises at least one detection assembly comprising:
    a deflection field device, for converting an incoming electron beam of mixed energy into an energy-resolved array of sub-beams;
    a selection grid, which can be electrified to a given potential so as to act as a high-pass filter for an electron flux directed at the grid;
    a multi-channel counter employing a semiconductor material in which an electrical current is stimulated by an electron impinging on the material, whereby current values thus measured are sorted and counted;
    and hybrids and combinations hereof.

5. The method of claim 1, wherein said electrons comprise backscatter electrons, secondary electrons, and combinations hereof.

6. The method of claim 1, wherein said deconvolution is performed with the aid of a mathematical technique selected from the group comprising:
    a Minimum Divergence method;
    a Maximum Entropy method;
    a Maximum À Posteriori method;
    a Linear Deconvolution method;
    in addition to hybrids hereof and combinations hereof.

7. The method of claim 6, wherein said deconvolution and spatial resolution of the measurement set M are performed by minimizing a statistical divergence between a detection model and the measurement set M, assumed subject to a noise model, whilst applying constraints to said detection model.

8. The method of claim 7, wherein the measurement set M is automatically processed in a manner comprising:
    defining a Point Spread Function that, for each value of n, has a kernel value $K_n$ representing a behavior of said beam of particulate radiation in a bulk of the sample as perceived by the detector arrangement for electron energy value $E_n$;
    defining an imaging quantity that, for each value of n, has a value $Q_n$ that is a multi-dimensional convolution of $K_n$ and V, such that $Q_n = K_n * V$; and for each value of n, computationally determining a minimum divergence $$\min D(O_n \| K_n * V)$$

between $O_n$ and $Q_n$, wherein one solves for V while applying constraints on the values $K_n$.

9. The method of claim 7, wherein said noise model comprises at least one of Poisson noise, Gaussian noise, hybrids hereof and combinations hereof.

10. The method of claim 6, wherein use is made of a Maximum Entropy technique in which the spatial variable V(x) at voxel position x is defined in terms of an Entropy Ent (V(x)) selected from the group comprising:
   a Shannon entropy, $Ent(V(x)) = \Sigma_x V(x) \cdot \log V(x)$;
   a Burg entropy, $Ent(V(x;)) = \Sigma_x \log V(x)$;
   in addition to hybrids hereof and combinations hereof.

11. The method of claim 6, wherein use is made of a regularization term in performing said deconvolution.

12. The method of claim 1, wherein:
   said steps of compiling a measurement set M and mathematically converting it into a corresponding result set R are comprised in a computational slicing step; and
   said computational slicing step is combined with a physical slicing step, whereby a physical material removal method is used to physically remove a layer of material from the original surface of the sample, thereby revealing a newly exposed surface of the sample.

13. A charged-particle microscope, comprising:
   a sample holder for holding a sample;
   a particle-optical column for directing at least one beam of particulate radiation onto a surface S of the sample, thereby producing an interaction that causes emitted radiation to emanate from the sample;
   a detector arrangement for detecting at least a portion of said emitted radiation comprising electrons;
   an electronic memory for recording an output $O_n$ of said detector arrangement as a function of kinetic energy $E_n$ of said electrons, thus compiling a measurement set $M = \{(O_n, E_n)\}$ for a plurality of values of $E_n$; and
   a computer processing apparatus for automatically deconvolving the measurement set M and spatially resolving it into a result set $R = \{(V_k, L_k)\}$, in which a spatial variable V demonstrates a value $V_k$ at an associated discrete depth level $L_k$ referenced to the surface S, whereby n and k are members of an integer sequence, and spatial variable V represents a physical property of the sample as a function of position in its bulk.

14. The charged-particle microscope of claim 13, wherein said detector arrangement is embodied to examine a plurality of substantially discrete energy values $E_n$, such that the measurement set M is compiled by simultaneously acquiring its component data pairs $(O_n, E_n)$, simultaneously or sequentially.

15. The charged-particle microscope of claim 13, wherein said detector arrangement comprises at least one detection assembly comprising:
   a deflection field device, for converting an incoming electron beam of mixed energy into an energy-resolved array of sub-beams;
   a selection grid, which can be electrified to a given potential so as to act as a high-pass filter for an electron flux directed at the grid;
   a multi-channel counter employing a semiconductor material in which an electrical current is stimulated by an electron impinging on the material, whereby current values thus measured are sorted and counted;
   and hybrids and combinations hereof.

16. The charged-particle microscope of claim 13, wherein said electrons comprise backscatter electrons, secondary electrons, and combinations hereof.

17. The charged-particle microscope of claim 13, wherein said deconvolution is performed with the aid of a mathematical technique comprising a Minimum Divergence method, a Maximum Entropy method, a Maximum À Posteriori method, and a Linear Deconvolution method, in addition to hybrids hereof and combinations hereof.

18. The charged-particle microscope of claim 17, wherein said deconvolution and spatial resolution of the measurement set M are performed by minimizing a statistical divergence between a detection model and the measurement set M, assumed subject to a noise model, whilst applying constraints to said detection model.

19. The charged-particle microscope of claim 18, wherein the measurement set M is automatically processed in a manner comprising:
   defining a Point Spread Function that, for each value of n, has a kernel value $K_n$ representing a behavior of said beam of particulate radiation in a bulk of the sample as perceived by the detector arrangement for electron energy value $E_n$;
   defining an imaging quantity that, for each value of n, has a value $Q_n$ that is a multi-dimensional convolution of $K_n$ and V, such that $Q_n = K_n * V$; and
   for each value of n, computationally determining a minimum divergence $\min D(O_n \| K_n * V)$ between $O_n$ and $Q_n$, wherein one solves for V while applying constraints on the values $K_n$.

20. The charged-particle microscope of claim 17, wherein use is made of a Maximum Entropy technique in which the spatial variable V(x) at voxel position x is defined in terms of an Entropy Ent (V(x)) selected from the group comprising:
   a Shannon entropy, $Ent(V(x)) = \Sigma_x V(x) \cdot \log V(x)$;
   a Burg entropy, $Ent(V(x)) = \Sigma_x \log V(x)$;
   in addition to hybrids hereof and combinations hereof.

* * * * *